United States Patent [19]

Glancy

[11] 4,202,327
[45] May 13, 1980

[54] DYNAMIC ORTHOTIC DEVICE

[76] Inventor: John J. Glancy, 6280 Dean Rd., Indianapolis, Ind. 46220

[21] Appl. No.: 908,967

[22] Filed: May 24, 1978

[51] Int. Cl.² ............................................. A61F 5/02
[52] U.S. Cl. ........................................ 128/78; 128/90
[58] Field of Search .................. 128/69, 78, 88, 89 R, 128/90

[56] References Cited

U.S. PATENT DOCUMENTS

| | | | |
|---|---|---|---|
| 67,333 | 7/1867 | Miller | 128/78 |
| 82,147 | 9/1868 | Netterfield | 128/78 |
| 492,903 | 3/1893 | Gerlitz | 128/78 |
| 2,723,664 | 11/1955 | Davis | 128/78 |
| 3,871,367 | 3/1975 | Miller | 128/78 |
| 4,057,056 | 11/1977 | Payton | 128/89 R |

FOREIGN PATENT DOCUMENTS 21246 9/1903 United Kingdom ..................... 128/78

OTHER PUBLICATIONS

Lovett et al., Treatment of Scoliosis, J.B. & J.S. 1924, pp. 848, 849.

*Primary Examiner*—Robert W. Michell
*Assistant Examiner*—Arthur S. Rose
*Attorney, Agent, or Firm*—Kirkland & Ellis

[57] ABSTRACT

This application discloses a dynamic orthosis device utilizing elastic forces to treat scoliosis or other curvatures of the spine. First and second shell segments are provided with a connecting arrangement for adjustably aligning them so as to encompass the torso. At least one pressure pad is pivotably mounted to one of the shell segments, and an elastic strap is adjustably secured to one of the shell segments so as to exert a predetermined force on the pressure pad. The elastic strap, pressure pad and shell segments cooperate to apply adjustable dynamic forces to correct abnormal curvatures of the spine.

8 Claims, 7 Drawing Figures

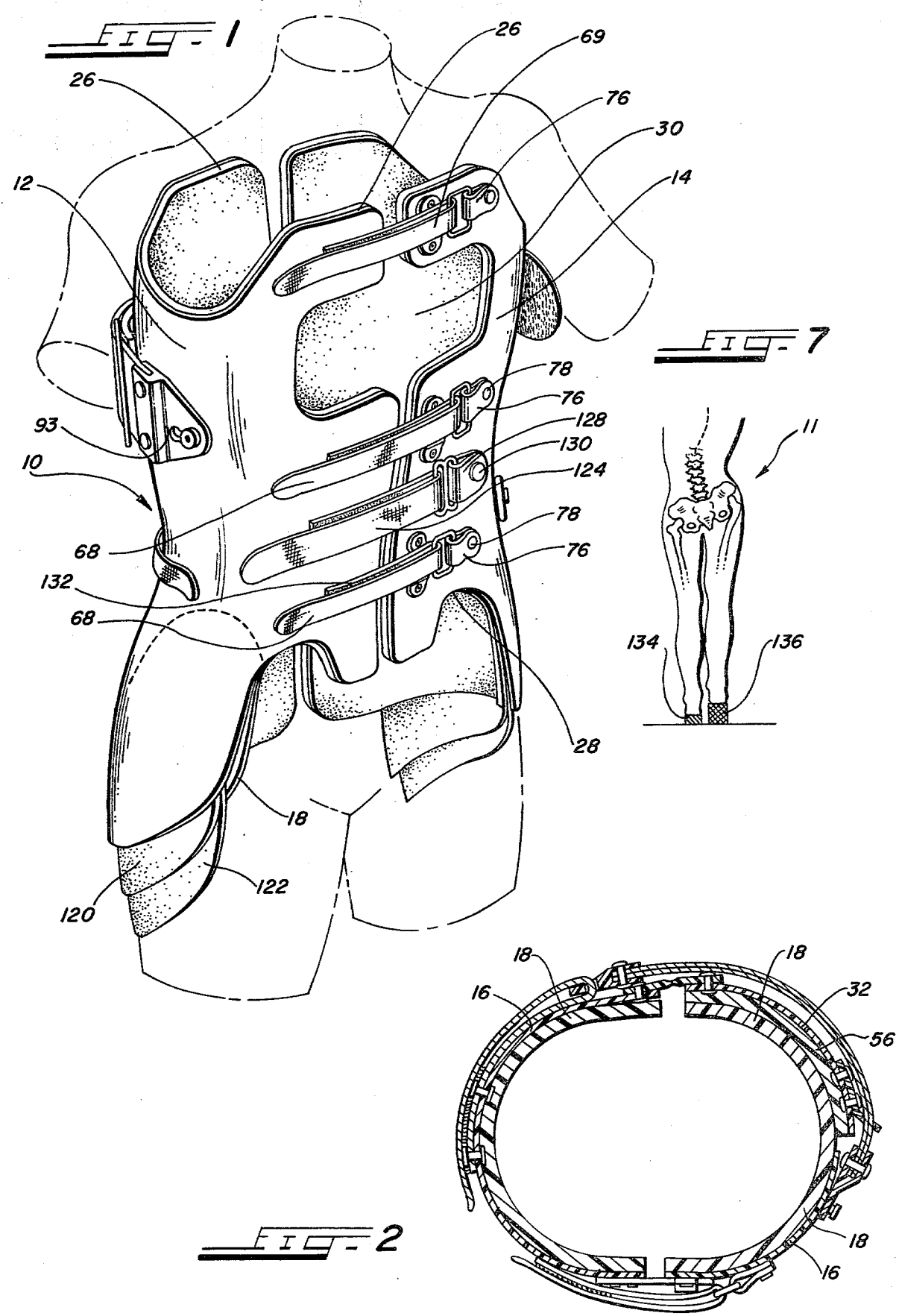

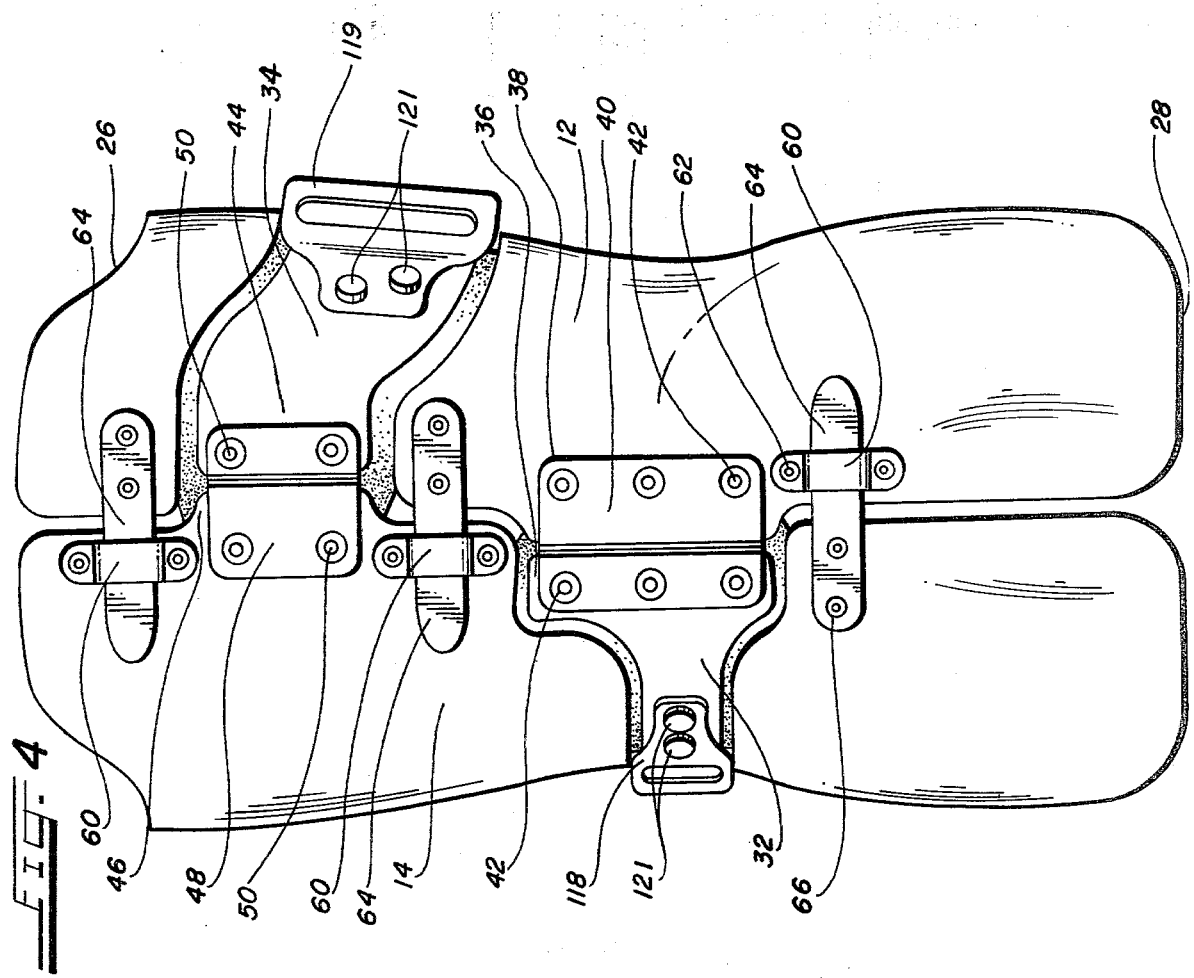
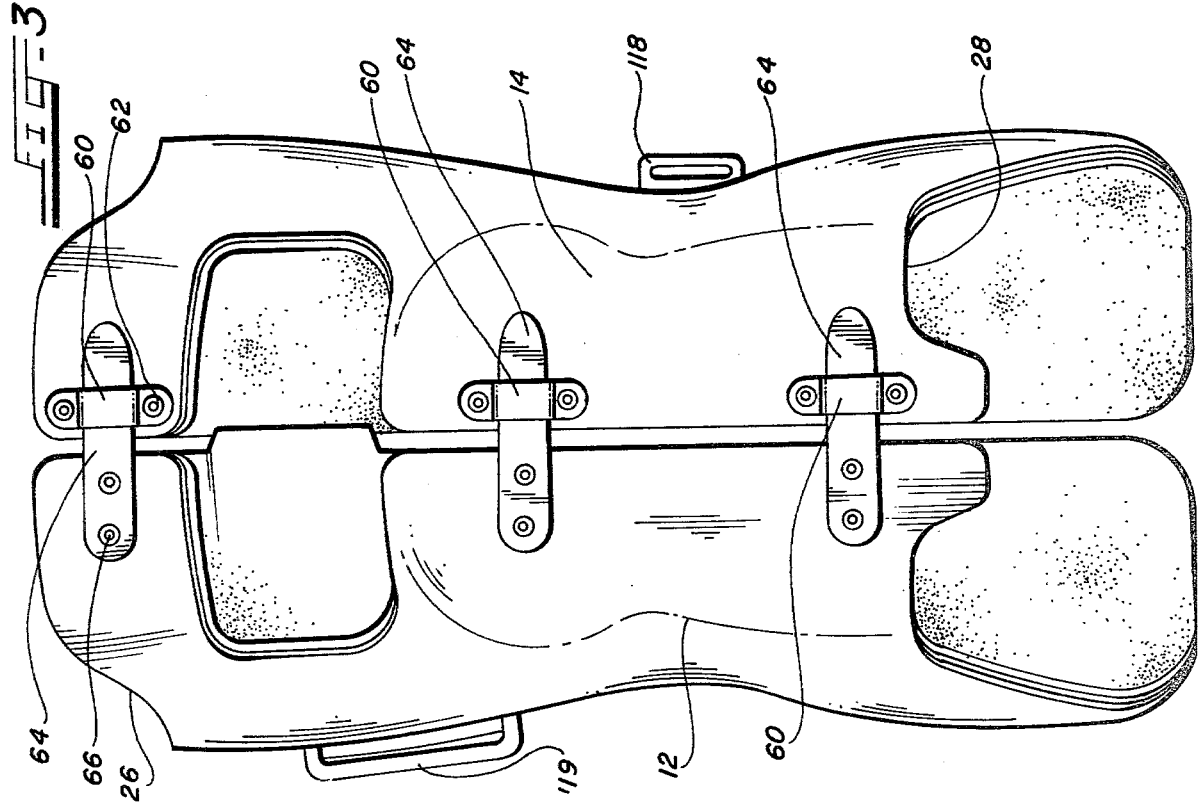

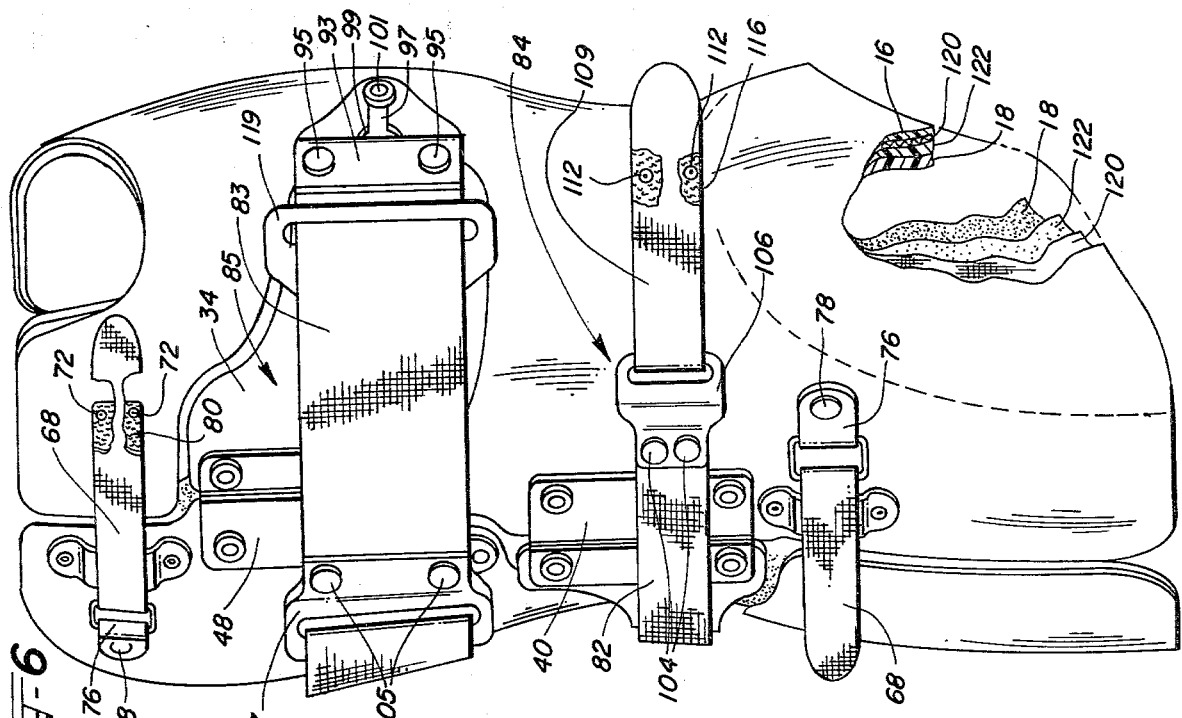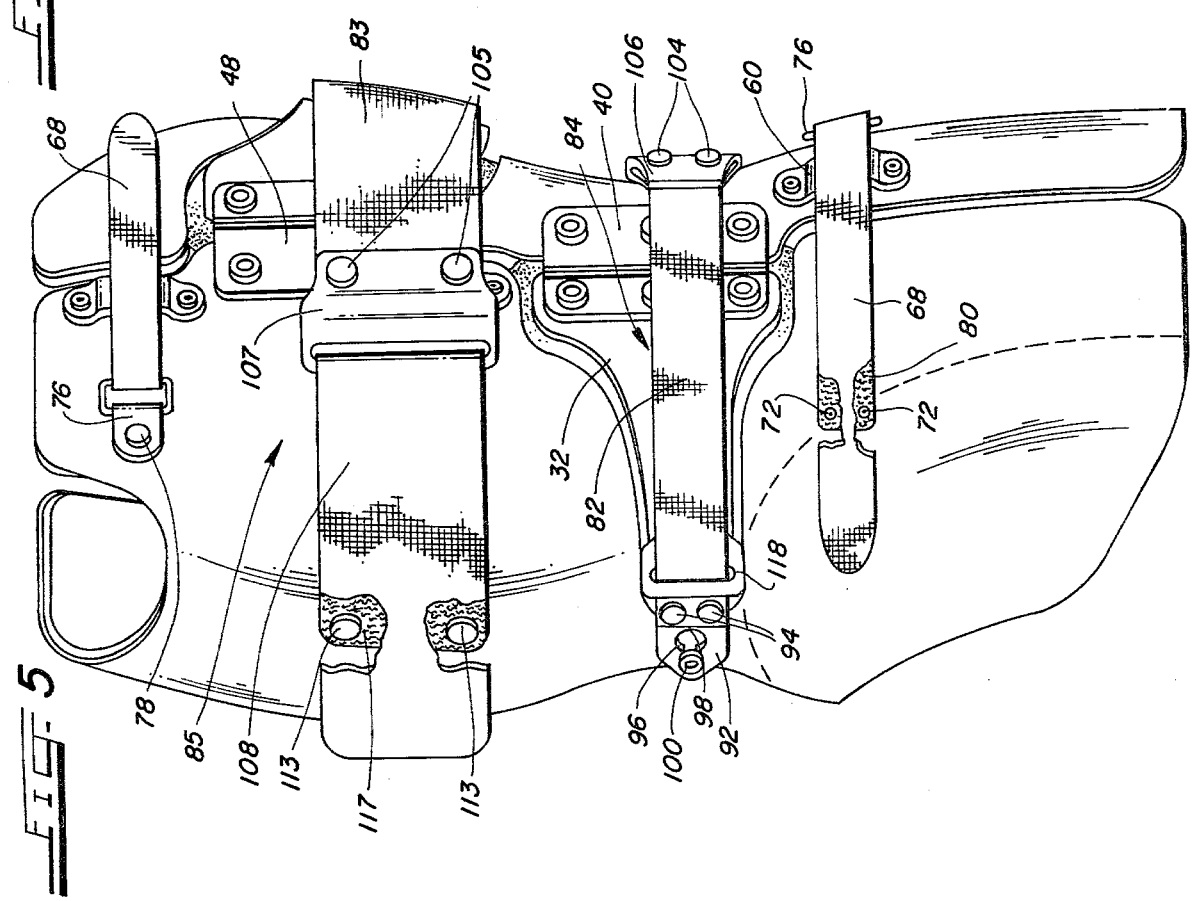

DYNAMIC ORTHOTIC DEVICE

BACKGROUND OF THE INVENTION

1. Field of the Invention

This invention relates to the non-operative or orthotic treatment of scoliosis, lordosis and kyphosis, and more particularly relates to the application of elastic forces to provide a dynamic orthotic device to treat scoliotic, lordotic and kyphotic conditions of the spinal column.

2. Description of the Prior Art

Heretofore, there have been various types of orthoses utilized in the treatment of scoliosis, lordosis, kyphosis, and other abnormal curvatures of the spine. However, these orthoses have been limited almost exclusively to static orthoses as opposed to dynamic orthoses which utilize elastic materials to generate dynamic external forces.

Static orthotic devices can be categorized as supportive, corrective or active corrective orthoses. The supportive types are used as a preventive measure to maintain the present status of a noncorrectable condition and to try to stop the condition from becoming more severe.

The corrective types are basically cylindrical forms that are shaped to as normal, or symmetric, a contour as the abnormal curvature allows. These devices usually completely encompass all portions of the trunk affected by the curvature. The effectiveness of this second category of devices is dependent upon the degree of suppleness or elasticity within the curvature which makes it possible to pre-position or realign an asymmetric spine and trunk into a more normal posture in order to match the symmetric contours of the device. The force to pre-position the trunk is generated by the patient's own muscularture as he puts on the device or is assisted into the device by another person.

The active corrective types of orthoses usually utilize a metal frame which is mounted upon an intimately fitting pelvic portion commonly referred to as the girdle. The frame portion usually extends the length of the spinal column and does not fit the trunk intimately. The frame's rigid structure is used for the attachment of various adjustable pressure pads by means of strapping. The space between the trunk and the surrounding frame allows for manipulation of the curvature by the elective positioning of various kinds of pressure pads to induce a reduction or correction of the curvature. The principal function of the pressure pads is to serve as a reminder to the wearer not to slump against the pads. Thus, the wearer must voluntarily and consciously use his trunk musculature to pull away from the pads thus actively correcting his curvature. Therefore, the amount of time during which the wearer responds to the device to actively correct the curvature is negligible compared to the amount of time that the device acts merely to maintain the status quo of his curvature.

In addition, since the voluntary motion of the spinal column by the wearer must be a conscious act, it follows that during sleep voluntary correction is not possible with a static orthotic device. Furthermore, it is not physically possible to voluntarily produce true corrective derotation in the transverse plane, because there is no physical way for the wearer to differentially rotate the individual vertebrae at will with the varying degree that is required for correction of a particular curvature.

The use of elastic materials as a source of external power can be useful in the development of a practical dynamic orthotic system for the correction of various deformities of the spine. Elastic materials can store and deliver significant amounts of dependable energy. They can be made to produce a continuous force that can be employed in a manner that creates an orthotic system with dynamic forces. The fact that these dynamic forces can be varied in magnitude and made to serve a variety of purposes allows a versatility that far exceeds that of static orthotic systems.

A dynamic orthotic device utilizing elastic materials as a source of external power can produce dynamic forces which are operative while the wearer is awake or asleep. This is important because when the wearer is asleep, the soft tissue surrounding the spinal column is in a relaxed state and the contracted tissue can yield to long-term dynamic pressure accurately directed to the immediate vicinity of the apex of curvature. However, at the same time the vertebral column must be held under firm control in order to prevent diffusion of the force in the form of unwanted lateral shifting of the column as a whole. By using this combination of dynamic pressure and firm control the reduction of the angle of the curvature at the site of the apex results in the overall elongation of the spinal column rather than lateral displacement. Furthermore, by providing the dynamic orthotic device with an adjustable mechanism, it is possible to adjust the device to maintain the correction attained during sleep.

Accordingly, the primary objective of this invention is to provide an efficient, automatic and practical dynamic orthotic system for the treatment of abnormal curvatures of the spine through the application of dynamic external forces generated by elastic materials.

Another objective is to provide a practical dynamic orthotic device which provides dynamic forces which are operative while the wearer is asleep, thereby achieving correction without conscious effort while the soft tissue surrounding the spinal column is in a relaxed state and can more easily yield to dynamic pressure.

Yet another objective is to provide a dynamic orthotic device whereby the dynamic force is applied to the immediate area about the apex of the curvature while holding the rest of the vertebral column under firm control in order to prevent diffusion of the force in the form of unwanted lateral shifting of the spinal column as a whole.

It is also an objective to provide a dynamic orthotic device wherein the external dynamic force also can be applied so as to effectuate a moment to derotate the abnormal transverse rotation that often occurs along with an abnormal curvature of the spine.

A related objective is to provide a dynamic orthotic device whereby the reduction of the angle of the curvature results in an overall elongation of the spinal column and not in lateral displacement.

A further objective is to provide a dynamic orthotic device which is adjustable in a manner which permits the overall mediolateral width of the unit to be gradually drawn in to maintain during the day the correction attained while the wearer was asleep.

A still further objective is to provide a dynamic orthotic device wherein the dynamic forces within the system are readily adjustable in order to facilitate correction of the curvature throughout the continuing long-term corrective process.

SUMMARY OF THE INVENTION

The foregoing and other objects, advantages and features of the present invention may be achieved with a dynamic orthotic device adapted for application to the torso of a patient with an abnormal curvature of the spine, comprising first shell means; second shell means; connecting means for aligning and adjustably connecting first and second shell means; pad means pivotably mounted to the shell means; elastic means capable of exerting a predetermined force on the pad means; and means for adjusting and securing the elastic means to the shell means; whereby, the elastic means provides adjustable dynamic forces which are applied to correct abnormal curvatures of the spine.

In use the dynamic orthotic device applies continuous readily adjustable dynamic forces directed precisely to the apex of the curvatures, and with the precise forces necessary to attain correction of a curvature of a given degree and/or location in the anteriorposterior, mediolateral and transverse planes simultaneously. Moreover, the device is adjustable so that the overall mediolateral width of the device may be gradually drawn in to maintain the correction achieved.

Accordingly, the device of this invention provides a practical dynamic orthotic system for the treatment of abnormal curvatures of the spine through the application of dynamic forces generated by elastic materials.

DESCRIPTION OF THE DRAWINGS

FIG. 1 is a perspective view of a patient wearing the dynamic orthotic device of this invention.

FIG. 2 is a horizontal section through the approximate center of the dynamic orthotic device of this invention.

FIG. 3 is a front elevational view of the dynamic orthotic device of this invention without the straps and elastic strapping installed.

FIG. 4 is a rear elevational view of the dynamic orthotic device of this invention without the straps and elastic strapping installed.

FIG. 5 is a left-side rear elevational view of the dynamic orthotic device of this invention.

FIG. 6 is a right-side rear elevational view of the dynamic orthosis device of this invention.

FIG. 7 is a rear elevational view showing the cushion heel lift.

DETAILED DESCRIPTION OF THE PREFERRED EMBODIMENTS

In accordance with the present invention a dynamic orthotic device is obtained which provides for the treatment of abnormal curvatures of the spine through the application of dynamic forces generated by elastic materials.

Referring to FIG. 1, there is shown a dynamic orthotic device 10 applied to a patient. The device 10 includes first and second shells 12, 14. FIG. 2 shows that the first and second shells 12, 14 are formed of a substantially rigid outer layer 16 of suitable material of about ⅛ to 3/16 inch thickness. Substantially any suitable material may be employed in fabricating the outer layer 16 of first and second shells 12, 14, but polypropylene has been found to be especially satisfactory. The rigid outer layer 16 of the first and second shells 12, 14 is lined with a compressible material 18 of about 3/16 to ¼ inch thickness. Substantially, any suitable material may be employed in fabricating the lining 18, but closed-cell polyethylene foam has been found to be especially satisfactory.

The dynamic orthotic device 10 may be advantageously formed and constructed by the following procedure. A plaster of Paris model of the patient's torso is first constructed. This torso model is then modified to achieve a symmetry of form to both sides of the torso model and to provide the indentations at the waist and flattening of the abdomen in accordance with state-of-art methods. The purpose of the symmetry of form is to draw the trunk into as normal a posture as the curvature will initially allow. The flattening of the abdomen and the waist indentations are means known in the art to be efficient at partially unweighting the lumbar region of the spinal column.

The lining 18 is formed on the modified torso model, and pieces of lining are bonded to the lining to form hollow pockets over the waist identations. A silastic elastomer is then poured into the hollow areas and the pockets are sealed. The rigid outer shell 16 is then formed over the lining 18. The outline of the top and bottom trim lines are drawn upon the rigid thoracopelvic shell. The thoracopelvic shell is then removed from the torso model and trimmed on the top 26 and bottom 28 to conform in general to the shape depicted in FIGS. 3 and 4.

On an X-ray film of the patient's torso, a reference line, perpendicular to the floor, is drawn through the center of the pelvis along the full length of the spinal column. This line simulates the midsagittal line of the body. The distance from the center of the body of the vertebra that forms the apex of the lateral curve to the reference is measured. If there is more than one curve, i.e., a compensating curve on the opposing side, the distance from the center of the body of the vertebra that forms the apex of each curve is measured in the same manner and the distances are added together. A vertical centerline is then drawn on the front and back of the thoracopelvic shell. In the case of a single curvature, the distance between the center of the body of the apical vertebra and the reference line of the X-ray film is divided in half and that amount is cut off both sides, front and back, of the centerlines drawn on the thoracopelvic shell. In the case of a multiple curvature, the sum of the distance between the apical vertebrae and reference line on the X-ray film are divided in half and the same procedure, just described, is followed.

The thoracopelvic shell has thus been cut into first and second shells 12, 14, and, when placed onto the torso model, the first and second shells 12, 14 leave a gap along the front and back centerline equal to the displacement of the spine shown on the X-ray film. The rationale for this arrangement is that the first and second shells 12, 14 can be drawn together to maintain the correction as the curvature is reduced.

In addition, from the x-ray, the size, shape and location of the corrective pressure pads is also determined. The outline of the corrective pressure pad, or pads, is drawn on the appropriate first or second shells 12, 14. The corrective pressure pad, or pads, are then cut out of the first and/or second shells 12, 14, leaving the soft compressible material 18 intact. The edges of the corrective pressure pads are then trimmed so that they are smaller than the cut-outs in the first and second shells 12, 14 out of which they came, in order to prevent any possible binding or overlap when remounted.

FIGS. 5 and 6 show first and second corrective pressure pads 32, 34 mounted to the first and second shells 12, 14, respectively of dynamic orthotic device 10. First corrective pressure pad 32, which was cut out of second shell 14, is attached at its medioposterior edge 36 to first shell 12 at the posterior portion 38 by means of a hinge 40. The hinge 40 is securely mounted to first corrective pressure pad 32 and first shell 12 by any suitable means such as rivets 42. Second corrective pressure pad 34, which was cut out of first shell 12, is attached at its medioposterior edge 44 to second shell 14 at the posterior portion 46 by means of a hinge 48. The hinge 48 is securely mounted to second corrective pressure pad 34 and second shell 14 by any suitable means such as rivets 50. With specific reference to FIG. 2, the inner surfaces of the first and second corrective pressure pads 32, 34 are covered with additional soft compressible material 56, 58, respectively.

It will be appreciated that first and second corrective pressue pads 32, 34, could also be mounted to second and first shells 14, 12, respectfully, out of which they were cut. Furthermore, while two corrective pressure pads have been described herein, it will be appreciated that any number of corrective pressure pads could be utilized.

FIGS. 3 and 4, show slotted receptacles 60 mounted on the front and rear of first and second shells 12, 14. Substantially, any suitable material may be employed in fabricating the slotted receptacles 60, but nylon has been found to be especially satisfactory. The slotted receptacles 60 may be mounted to first and second shells 12, 14 by any suitable means such as rivets 62.

Alignment bars 64 adapted to slidably fit within slotted receptacles 60 are mounted horizontally opposed on the opposing first or second shells 12, 14 adjacent to slotted receptacles 60. Substantially, any suitable material may be employed in fabricating the alignment bars 64, but aluminum has been found to be especially satisfactory. The alignment bars 64 may be mounted to first and second shells 12, 14 by any suitable means such as rivets 66.

The alignment bars 64 and slotted receptacles 60 in combination connect the first and second sides 12, 14 to form a dynamic orthotic device 10 which encompasses the trunk and provides for as little unwanted front and rear and up and down relative motion between the first and second shells 12, 14 as possible.

FIGS. 1, 5 and 6, show straps 68, 69 which secure the first and second shells 12, 14 together. The straps 68, 69 pass over each of the alignment bars 64 and slotted receptacles 60. Straps 68, 69 are secured to either first or second shells 12, 14 by any suitable means such as rivets 72. Straps 68, 69 then pass through loop pieces 76 which are secured to the opposing first or second shell 12, 14 by any suitable means such as rivets 78. Straps 68, 69 are fastened to the first or second shells 12, 14 to which straps 68, 69 are secured by any suitable means such as a Velcro fastener 80.

In addition, there can be provided an elastic member in strap 69 which passes over the alignment bar above the open-chest cutout 30. The elastic member in strap 69 in conjunction with the open-chest cutout 30 facilitates the chest expansion associated with breathing.

Elastic strappings 82, 83 provide the dynamic force and are utilized in pull straps 84, 85, respectively, which are positioned so as to cross horizontally over the entire length of the outer surfaces of the first and second corrective pressure pads 32, 34, respectively. Any convenient elastic material may be used, but it is preferred to employ single or multiple plys of woven elastic strapping about 1 to 3 inches wide. Other suitable elastic materials may be used, such as rubber members, springs, and the like.

FIGS. 5 and 6 show how the pull straps 84, 85 are mounted on the dynamic orthosis device 10. Substantially any suitable means of mounting the pull straps 84, 85 could be employed, but the method described herein has been found to be particularly convenient for ease of attachment, removal and adjustment.

The elastic strappings 82, 83 are secured to mounting plates 92, 93, respectively, by any suitable means such as rivets 94, 95. Mounting plates 92, 93 have slots 96, 97 with enlarged openings 98, 99 provided at one end thereof. The mounting plates 92, 93 are fastened to first and second shells 12, 14, respectively, by means of studs 100, 101 which are permanently affixed to first and second shells 12, 14, respectively. Studs 100, 101 are inserted through enlarged openings 98, 99 and slidably positioned in slots 96, 97 of mounting plates 92, 93.

The elastic strappings 82, 83 pass through slotted keepers 118, 119, respectively, which are secured to the first and second corrective pressure pads 32, 34 by any suitable means such as rivets 121. The purpose of slotted keepers 118, 119 is to insure that the elastic strappings 82, 83 do not slip off the first and second corrective pressure pads 32, 34.

The elastic strappings 82, 83 are secured by any suitable means such as rivets 104, 105 to slotted end pieces 106, 107, respectively, adapted to receive straps 108, 109. Straps 108, 109 are secured to the opposing first or second shells 12, 14 from which the elastic strapping 82, 83 is secured by any suitable means such as rivets 112, 113. Straps 108, 109 pass through the slotted end pieces 106, 107, respectively, and are adjustably fastened near or to its secured end by any suitable means such as Velcro fasteners 116, 117.

FIGS. 1 and 6 shows two removable pads, 120, 122 which can be incorporated into the first and second shells 12, 14 between the lining 18 and the rigid outer layer 16. They may advantageously be made of 1/16 to ¼ inch thick firm compressible material such as closed-cell polyethylene foam. Selection of the thickness of these pads is dependent upon the severity of the curvature and/or the age of the patient.

FIG. 1 shows an elastic balancing strap 124 which can be utilized with the dynamic orthotic device 10. The balancing strap 124 is secured to either first or second shell 12, 14 by any suitable means such as rivets 126. Balancing strap 124 passes through loop piece 128 which is secured to the opposing first or second shell 12, 14 by any suitable means such as rivet 130. Balancing strap 124 is adjustably fastened to the first or second shell 124, 14 to which balancing strap 12 is secured by any suitable means such as Velcro fastener 132. The tension of this balancing strap 124 is set to approximate the force acting to draw the first and second shells 12, 14 together.

In use the effect of the dynamic orthotic device 10 upon a given curvature is threefold: (1) because the corrective pressure pads 32, 34 are hinged along their medioposterior edges 36, 44, the resultant forces are converted to a dynamic moment that derotates the curvature; (2) due to the placement of the elastic strapping 82, the same resultant force generated by it is used to apply a dynamic inward thrust to the corrective pressure pads 32, 34 which act to reduce the lateral angle of the curvature at its apex; and (3) the same force that is generated by the elastic strapping 82 is utilized dynamically to draw both first and second shells 12, 14 together, thus resulting in an overall elongation of the spinal column by preventing the force being directed to the apex from being dissipated by unwanted lateral shifting of the overall spinal column.

Pads 120, 122 provide a means to retain the rigidity between the rib cage and the pelvis and still accommodate for the variance in mediolateral width between the torso as the spinal column corrects, and the relatively fixed diameter of the pelvis. As the spinal column elongates, the pads 120, 122 can be removed in any order desired, thus ensuring a continuous, positive influence along the thoracic spinal column. When correction has been achieved, the system is worn as a prophylactic during the remaining period of bony growth. Also, during the prophylactic period the removable pads 120, 122 can be utilized to accommodate the maturing pelvis as its mediolateral width broadens.

The elastic balancing strap 124 acts to prevent the first and second shells 12, 14 from tending to migrate around the trunk to the center of the back.

Thus, with the above interplay of dynamic forces, it is possible to effect a continuous, positive influence upon any given curvature for any period of time desired. Furthermore, the dynamic forces are readily adjustable so that the precise force necessary to attain correction of a curvature of a given degree and/or location can be applied. In addition, the dynamic orthotic device also operates as an efficient static or holding device during the daytime.

FIG. 7 shows a cushion heel lift system 11 which may be advantageously used as an adjunct to the dynamic orthotic device 10 shown in FIG. 1 to better maintain the correction of the curvatures obtained, against the destructiveness of floor reaction forces. This effect is achieved by adding a ¼ to 1 inch solid heel lift 134 under the heel on the convex side of the curvature, and a cushion heel lift 136, equal to the solid heel lift plus an additional thickness equal to the pelvic oliqueness, under the heel on the concave side of the curvature. The thickness of the solid heel lift depends on the degree of pelvic obliquity and the tightness, or severity, of tissue contracture on the concave side of the lumbar curvature.

FIG. 7 shows a left lumbar curve with an oblique pelvis. The hip on the concave, or right side, has been drawn upward with apparent shortening of the right leg. The weight of the trunk being borne by the spinal column is transferred to the pelvis, which is supporting the spinal column, at which point the burden is equally divided and continues downward to the floor, via the skeletal structure of the legs. By the time contact with the floor has been made, the weight of the pelvis and each leg has been added to the vertical load that each foot must carry.

The patient must compensate for the lumbar curve and oblique pelvis by flexing the knee on the convex side of the curvature so that the foot on the concave side can contact the floor and allow each leg to bear an equal share of the body's weight. However, this compensation does not correct the abnormal position of the oblique pelvis, and the net effect is for the floor reaction forces to maintain the oblique pelvis.

The use of a cushion heel can manipulate these floor reaction forces. the dynamic orthotic device 10 and the cushion heel lift system 11 can in time achieve correction of the oblique pelvis. When the cushion heel lift system 11 is first applied, the right hip will be much as shown in FIG. 7, but with a slight compression of the cushion heel lift 136. As the dynamic orthotic device begins to reduce and derotate the curvature the cushion heel lift 136 allows the hip on the concave side to become parallel with the ground gradually as the contracted tissues respond to the dynamic forces.

Accordingly, the dynamic orthotic device of this invention thus fulfills a significant role in overcoming the disadvantages of prior art efforts employing only static control. In particular, it provides a practical dynamic orthotic device for the treatment of abnormal curvatures of the spine through the application of dynamic forces generated by elastic materials.

In addition, the dynamic orthotic device provides dynamic forces which are operative while the wearer is asleep and while the soft tissue surrounding the spinal column is in a relaxed state and can more easily yield to dynamic pressure. At the same time the device is capable of applying the dynamic force to the immediate area about the apex of the curvature while holding the rest of the vertebral column under firm control in order to prevent diffusion of the force in the form of unwanted lateral shifting of the spinal column as a whole. Thus, the reduction of the angle of the curvature results in an overall elongation of the spinal column and not in lateral displacement.

Furthermore, the dynamic forces generated by the device of this invention are readily adjustable in order to attain correction of a curvature of a given degree and/or location, while at the same time effectuating a derotation of the abnormal curvature. Moreover, the dynamic orthotic device of this invention is adjustable in a manner which permits the overall mediolateral width of the device to be gradually drawn in to maintain the correction achieved.

I claim:

1. A dynamic orthosis device adapted for application to the torso of a human patient with an abnormal curvature of the spine comprising:

substantially rigid torso-enveloping shell means split vertically at anterior and posterior positions to form first and second shell segments;

connecting means for gradually drawing said shell segments together and for securing said shell segments in any of a plurality of positions relative to one another, alignment means for restricting said shells to horizontal relative movement while they are gradually drawn together, at least one portion of a shell segment being cut-away and pressure pad means being positioned in the cut-away portion and pivotally attached to the other shell segment;

elastic strap means secured at one end to the shell means and operatively associated with each pressure pad means; and means for adjustably securing the elastic strap means to the shell means adjacent the other end of the strap means such that it exerts an adjustably predetermined dynamic force on its associated pressure pad means;

whereby the elastic means causes the pressure pad means to apply adjustable predetermined dynamic forces to the patient's torso in order to correct abnormal curvatures of the patient's spine.

2. A device, as claimed in claim 1, wherein the first and second shell segments are separated by a distance substantially equaling the maximum abnormal curvature of the spine.

3. A device, as claimed in claim 1, wherein the first and second shell segments comprise rigid means generally conforming to the patient's torso and lined with soft compressible material and are adapted to conform to and engage the torso.

4. A device, as claimed in claim 1, wherein the alignment means comprises horizontal alignment bars secured to one of the shell segments, receptacles secured to the other shell segment, each adapted slidably to receive one of the alignment bars, and wherein the connecting means comprises non-elastic strap means provided with adjustable fastening means for securing the shell segments in aligned position whereby the dynamic forces exerted by the elastic means cooperate with gravitational forces to exert predetermined dynamic forces while the patient is at rest.

5. A device, as claimed in claim 1, wherein a pressure pad means is formed from a cut-away portion of each of the shell segments.

6. A device, as claimed in claim 1, further comprising removable pad means adapted to be inserted into the lateral pelvic portions of the first and second shell segments.

7. A device, as claimed in claim 1, further comprising anterior elastic balancing strap means horizontally connecting to the first and second shell segments.

8. A method of treating abnormal curvatures of the spine of a human patient while at rest as well as when awake comprising the step of exerting dynamic external forces on the spine by applying to the torso of the patient the dynamic orthosis device of claim 1.

* * * * *